US00PP34163P2

(12) United States Plant Patent
Watters

(10) Patent No.: US PP34,163 P2
(45) Date of Patent: Apr. 26, 2022

(54) PLUM TREE NAMED 'GW1'

(50) Latin Name: *Prunus salicina*
Varietal Denomination: GW1

(71) Applicant: Vitaplum Technology Pty Ltd, Melbourne (AU)

(72) Inventor: Graeme Watters, Laanecoorie (AU)

(73) Assignee: Vitaplum Technology Pty Ltd, Melbourne (AU)

( * ) Notice: Subject to any disclaimer, the term of this patent is extended or adjusted under 35 U.S.C. 154(b) by 0 days.

(21) Appl. No.: 17/300,073

(22) Filed: Mar. 1, 2021

(51) Int. Cl.
*A01H 5/08* (2018.01)
*A01H 6/74* (2018.01)

(52) U.S. Cl.
USPC ..... Plt./184
CPC ..... *A01H 6/7472* (2018.05)

(58) Field of Classification Search
USPC ..... Plt./184
CPC ..... A01H 6/7472; A01H 5/08
See application file for complete search history.

(56) References Cited

PUBLICATIONS

O'Callaghan, FruitNet, Asia Fruit, Aug. 6, 2020.*

* cited by examiner

*Primary Examiner* — Keith O. Robinson
(74) *Attorney, Agent, or Firm* — Michelle Bos Legal LLC

(57) ABSTRACT

A Japanese plum variety named 'GW1' notable for its very late harvest maturity and its intensely colored fruit.

4 Drawing Sheets

Genus and species: *Prunus salicina.*
Variety denomination: 'GW1'.

CROSS-REFERENCE TO RELATED APPLICATIONS

None

STATEMENT REGARDING FEDERALLY SPONSORED RESEARCH OR DEVELOPMENT

None

BACKGROUND AND SUMMARY OF THE VARIETY

The new Japanese plum variety 'GW1' originated as a chance seedling of the variety 'Ruby Blood' plum (not patented) discovered on the breeder's property at Laanecoorie, Victoria, Australia in 2011. In June 2012, the dormant seedling was replanted in the breeder's orchard at Laanecoorie. The seedling was grown and maintained in the breeder's orchard during the summers of 2012/13 to 2016/17 where the first fruit was seen on the seedling tree in late March 2017. The tree was observed to produce very late-maturing, large, sweet fruit with very dark skin and flesh. 'GW1' was first asexually propagated in 2017 by stick grafting onto 'H29C' rootstock (not patented), and has been found to be stable and to retain its distinctive characteristics over successive asexually propagated generations.

'GW1' has been compared to and can be distinguished from parent variety 'Ruby Blood' and related varieties 'Suplumfifty' (U.S. Plant Pat. No. 27,327) and 'Queen Garnet' (U.S. Plant Pat. No. 19,630). The fruit of 'GW1' is larger, sweeter, and has markedly darker skin than that of 'Ruby Blood.' The fruit of 'GW1' ripens late- to very late-season, compared to medium- to late-season for 'Queen Garnet' and 'Suplumfifty.' 'GW1' has been observed to exhibit substantially higher levels of beta carotene, anthocyanins and antioxidants as compared to 'Queen Garnet.'

The 'GW1' plum tree has been found to retain and exhibit its distinctive characteristics through successive asexually propagated generations.

BRIEF DESCRIPTION OF THE PHOTOGRAPHS

The accompanying photographs were obtained in February 2021 at Shepparton East, Victoria, Australia. The trees depicted are 3 years old.

Figure 1:
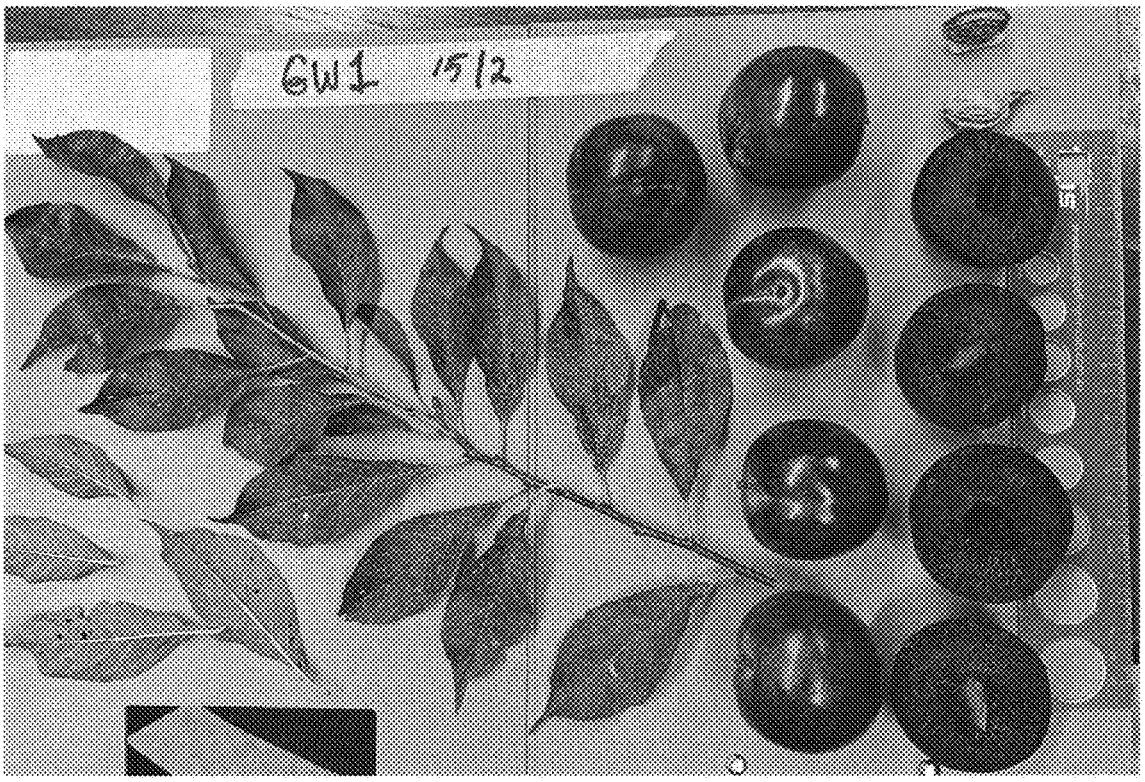
FIG. 1 shows a branch, leaves, whole fruit, sectioned fruit and stones of the 'GW1' variety.
Figure 2:
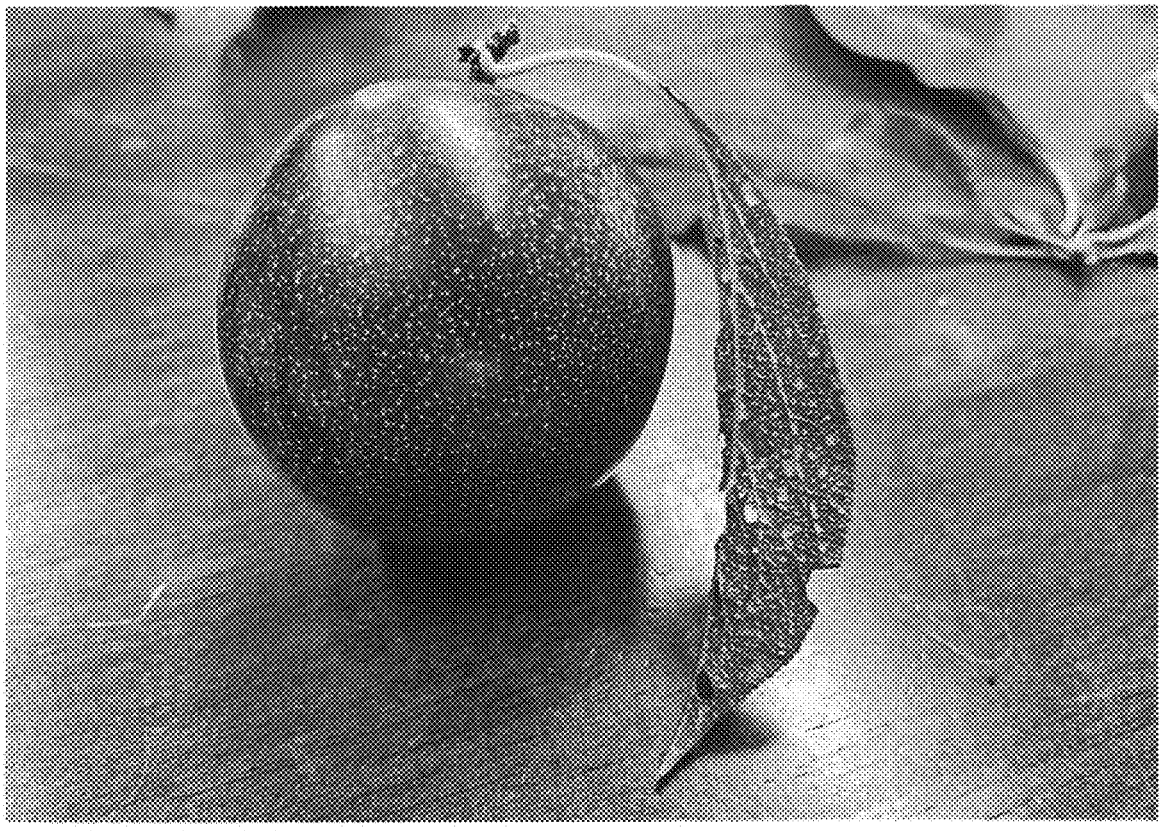
FIG. 2 shows a fruit of the 'GW1' variety.
Figure 3:
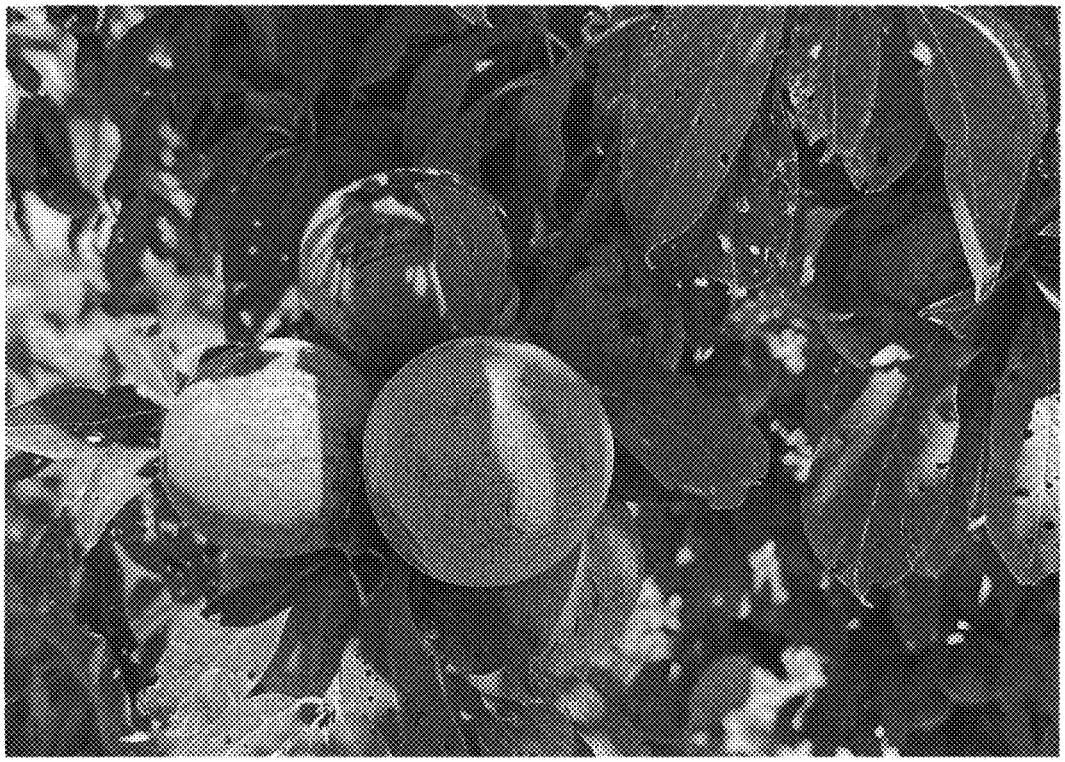
FIG. 3 shows leaves and fruit of the 'GW1' variety.
Figure 4:
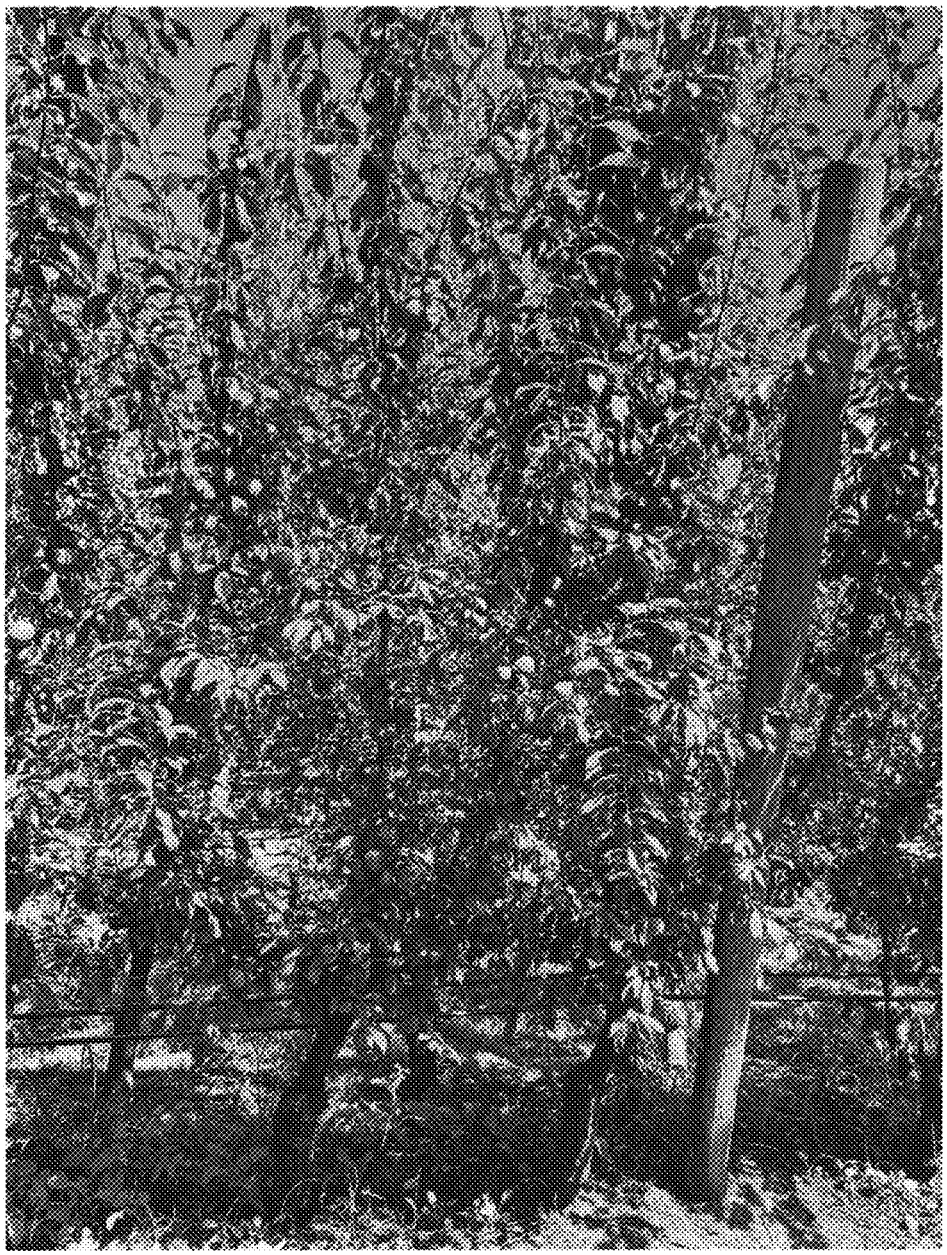
FIG. 4 shows a tree of the 'GW1' variety.

The colors shown in these photographs may vary with lighting conditions. Color characteristics of the claimed variety should therefore be determined with reference to the observations described herein, rather than from the photographs alone.

DETAILED BOTANICAL DESCRIPTION

The following detailed botanical description is based on observations of second-generation trees of the variety, grafted onto 'H29C' Myrobalan plum rootstock (not patented) in 2017. Observations were recorded during the 2017 through 2021 growing seasons near Shepparton East, Victoria, Australia. The characteristics described will vary somewhat depending upon cultural practices and climatic conditions, and can vary with location and season. Quantified measurements are expressed as an average of measurements taken from a number of individual plants of the new variety. The measurements of any individual plant, or any group of plants, of the new variety may vary from the stated average. Color descriptions are made with reference to The R.H.S. Colour Chart, fifth edition (Royal Horticultural Society, London).

Tree:

*Size*.—Height approximately 3.4 m to top of flushing branches; spread approximately 1.2 m at top of fruit load position (measurement at end of 3$^{rd}$ leaf season).

*Vigor*.—Moderate vigor.

*Habit, shape*.—Semi-spreading, rounded.

*Density*.—Moderately dense.

*Productivity*.—Moderate to high crop load.

*Bearing*.—Potential for biannual bearing.

*Number of picks*.—Single pick.

Trunk:

*Diameter*.—4.6 cm to 7.9 cm at 30 cm above graft union (measurement at end of 3rd leaf season).

*Lenticels*.—Horizontal lenticels, 3.0 to 6.3 mm long, 0.9 to 1.0 mm wide.

*Texture*.—Rough and peeling, typical of plum varieties.

*Color*.—Brown 200C.

Branches:

*Terminal shoot length*.—1.6 m.

*Diameter at base of terminal shoot*.—9.7 mm.

*Diameter at end of terminal shoot*.—2.6 mm.

*Primary scaffold branch diameter at base*.—41 mm.

*Secondary scaffold branch diameter at base*.—26 mm.

*Fruit hanging limb diameter at base*.—8 mm.

*Fruiting spur diameter at base*.—3.5 mm.

*Texture*.—Smooth on first year wood; increasing roughness with tree age.

*Lenticels on 2 year old wood*.—6 to 7 per cm$^2$, arranged horizontally.

*Lenticel size*.—1.8 mm to 4 mm long; 0.6 mm to 1.4 mm wide on 2 year old wood.

*Attitude of one year old shoot*.—Semi-erect.

*Color of new wood*.—Grey-brown 199A.

*Internode length on current season shoots*.—24 mm.

*Fruiting position on tree*.—On spurs and whip branches.

*Branch crotch angle*.—Average of 53° at 1 m above graft union.

*One year old shoot color*.—Greyed-orange 166A.

*One year old shoot lenticel color*.—Greyed-orange 167C.

*Fruiting branch color*.—Greyed-orange 176D.

*Fruiting branch lenticel color*.—Orange 26A.

Flowers:

*Time of beginning of flowering*.—Early; Late August to early September (2021).

*Pedicel length*.—6 mm to 8 mm.

*Sepal shape*.—Ovate.

*Petal shape*.—Elliptic.

*Petal length*.—9 mm to 11 mm.

*Petal width*.—7 mm to 9 mm.

*Petal color*.—White 155C.

*Petal texture*.—Smooth.

*Petal margin*.—Entire, mildly undulate.

*Position of stigma in relation to anthers*.—Above.

Leaves:

*Arrangement*.—Alternate.

*Attitude in relation to shoot*.—Horizontal.

*Length*.—10.2 cm.

*Width*.—4.7 cm.

*Form*.—Obovate.

*Apex*.—Acuminate.

*Angle of apex*.—Acute.

*Base*.—Acute.

*Margin*.—Serrate.

*Venation*.—Reticulate.

*Texture of upper surface*.—Glabrous.

*Color—upper surface*.—Green 137A.

*Color—lower surface*.—Yellow-green 146C.

*Petiole length*.—16.8 mm.

*Petiole diameter*.—2.4 mm.

*Petiole color*.—Greyed-green 195A.

*Petiole glands*.—2 to 3 globose glands in alternate arrangement on upper portion of petiole near base of leaf; Greyed-orange 167A.

*Stipules*.—Absent or non-conspicuous.

Fruit:

*Maturity*.—Late to very late.

*Size*.—Large.

*Weight*.—87 g.

*Length*.—53 mm.

*Diameter at widest point*.—53 mm.

*Form, viewed from apex*.—Round to ovate.

*Form, viewed from suture side*.—Occasionally slightly asymmetrical.

*Form, viewed from side perpendicular to suture*.—Occasionally slightly asymmetrical.

*Suture depth*.—2.3 mm.

*Stalk cavity depth*.—4.8 mm.

*Stalk cavity diameter*.—6.0 mm.

*Base shape*.—Slightly flat on shoulders.

*Apex shape*.—Slightly pointed.

*Stem length*.—10.7 mm.

*Stem diameter*.—1.9 mm.

Fruit flesh:

*Firmness*.—Very firm, Average 2.5 kgf.

*Texture*.—Fine, fibers inconspicuous.

*Flavor*.—Sweet with mild acidity.

*Juiciness*.—35% to 40% juice content.

*Brix*.—17.6%.

*Stone to flesh ratio*.—1:25.

*Aroma*.—Moderately strong.

*Flesh color*.—Greyed-purple 187A.

*Juice color*.—Greyed-purple 187B.

Fruit skin:

*Thickness*.—Medium.

*Texture*.—Smooth, glabrous and shiny upon brushing.

*Bloom wax*.—Heavily present on fruit at harvest.

*Ground color*.—Red 53A.

*Overall color*.—Greyed-purple 187A.

*Taste*.—Balanced sweet with low acidity.

*Lenticel quantity*.—More than 70 per cm$^2$.

*Lenticel shape*.—Round.

*Lenticel size*.—0.1 mm to 0.4 mm diameter.

*Lenticel color*.—White 155A to yellow-orange 17A.

Stone:

*Type*.—Semi-freestone.

*Length*.—25 mm.

*Width*.—18 mm.

*Shape*.—Sub-globular in ventral view; Long elliptical in basal view.

*Sides*.—Profile view asymmetrical; Ventral view symmetrical.

*Surface texture*.—Small pits throughout, including on blade.

*Ridges*.—Blade on suture can be complete or partial.

*Color*.—Greyed-orange 167A.

*Tendency to split*.—No splitting observed.

Use: Fresh consumption; high antioxidant health market; juice.

The invention claimed is:

1. A new and distinct variety of plum tree named 'GW1', substantially as illustrated and described herein.

* * * * *